United States Patent
Friese et al.

[11] Patent Number: 6,096,181
[45] Date of Patent: Aug. 1, 2000

[54] SEALING ELEMENT FOR A SENSOR

[75] Inventors: Karl-Hermann Friese, Leonberg; Helmut Weyl, Schwieberdingen; Hans-Martin Wiedenmann; Anton Hans, both of Stuttgart, all of Germany

[73] Assignee: Robert Bosch GmbH

[21] Appl. No.: 09/091,198

[22] PCT Filed: Sep. 26, 1997

[86] PCT No.: PCT/DE97/02197

§ 371 Date: Jan. 6, 1999

§ 102(e) Date: Jan. 6, 1999

[87] PCT Pub. No.: WO98/15820

PCT Pub. Date: Apr. 16, 1998

[30] Foreign Application Priority Data

Oct. 10, 1996 [DE] Germany ............................ 196 41 809

[51] Int. Cl.[7] .................................................. G01N 27/407
[52] U.S. Cl. ...................... 204/424; 204/427; 204/428; 277/650; 277/936; 277/939; 277/940; 277/941
[58] Field of Search .................................. 204/421–429; 277/650, 936, 939, 940, 941

[56] References Cited

U.S. PATENT DOCUMENTS

| | | | |
|---|---|---|---|
| 1,338,617 | 4/1920 | Fitzgerald | 277/941 |
| 3,923,667 | 12/1975 | Lachman | 277/941 |
| 4,088,555 | 5/1978 | Kita et al. | 204/428 |
| 4,139,376 | 2/1979 | Erickson et al. | 277/941 |
| 4,339,320 | 7/1982 | Friese et al. | 204/428 |
| 4,878,678 | 11/1989 | Hensley et al. | 277/941 |
| 5,690,800 | 11/1997 | Friese et al. | 204/424 |
| 5,698,084 | 12/1997 | Weyl et al. | 204/427 |

FOREIGN PATENT DOCUMENTS

| | | |
|---|---|---|
| 43 42 731 | 2/1995 | Germany . |
| 94 09 684 | 10/1995 | Germany . |
| 44 47 306 | 7/1996 | Germany . |

OTHER PUBLICATIONS

R.G. Delagi et al. "High–Aluminum Ferritic Stainless Alloys Synthesized For Catalytic Converters" Advanced Materials and Processes, pp. 27–28 (Jan. 1995).

Primary Examiner—T. Tung
Attorney, Agent, or Firm—Kenyon & Kenyon

[57] ABSTRACT

An electrochemical sensor for determining the oxygen content of gases of internal combustion engines includes a ceramic element that is inserted with a sealing ring into a housing. The sealing ring is built up from different metal layers. The arrangement of the metal layers proceeds from a metal support which is composed of a steel alloy. The sealing ring is covered on both sides with a roll-clad copper layer. A nickel layer can additionally be arranged beneath the copper layer.

13 Claims, 2 Drawing Sheets

SEALING ELEMENT FOR A SENSOR

BACKGROUND INFORMATION

The present invention relates to a seal for a sensor element having a ceramic element in the form of a solid electrolyte element embodied as a closed tube and fastened in a sealable manner to a metallic housing. The seal of the present invention is implemented between the solid electrolyte element and the housing.

German Published Patent Application No. 43 42 731 describes sensors based on solid electrolytes in which electrically conductive metal or graphite sealing rings are used for sealed immobilization of the solid electrolyte element in the housing. The metal sealing rings are moreover often covered with a galvanically deposited copper layer. At elevated temperatures, this leads to oxidation and corrosion of the metal or graphite surface. It can moreover cause the metal ions which are thereby created to diffuse into the solid electrolyte or into layers which are arranged on the surface of the solid electrolyte, such as conductive paths, cover layers, and insulation layers. This modifies and impairs their properties in terms of proper function.

SUMMARY OF THE INVENTION

According to the present invention, a sensor is provided that has the advantage that temperature- and corrosion-resistant sealing elements which have a highly ductile roll-clad surface layer of a metal can be used to seal the ceramic element, which may be in the form of a solid electrolyte element embodied as a tubular element. Because of the deformability of the compact seal, the sealing element rests with zero clearance against, in particular, the surface of the ceramic element. This ensures that even under extreme thermal conditions, corrosive substances cannot gain access to the rear portion of the solid electrolyte element and the contacts arranged there, and impair their properties. As compared with conventional galvanically applied metal layers, the advantage of roll-clad metal layers, in addition to their elevated ductility, is that they have a more uniform surface structure, possess no defects, and have a uniform layer thickness. They are moreover much more highly densified, which reduces the surface area for oxygen access. This results in a far lower leakage rate for seals which use sealing rings having roll-clad metal layers than for sealing rings having metal layers which were applied galvanically. A further advantage of roll-clad layers consists in the higher degree of automation in their manufacture as compared with galvanically applied layers and, associated therewith, a continuous process control of the layer thickness. This means that sealing rings produced in this manner have precisely reproducible quality with very close tolerances. As a result, the cost per item, in particular, can be decisively lowered.

An additional roll-clad nickel layer that is applied beneath the copper layer and faces toward the ceramic element allows even greater ductility for the combined copper and nickel layer, which compensates for the surface roughness ($R_{max}$ as defined by DIN 4768) and shape error of the ceramic element. Partial oxidation of the copper layer is desirable in order to improve the sealing capability of the sealing ring even further. This is achieved by means of a heat pretreatment, preferably at approximately 550 degrees.

DETAILED DESCRIPTION

Figure 1:
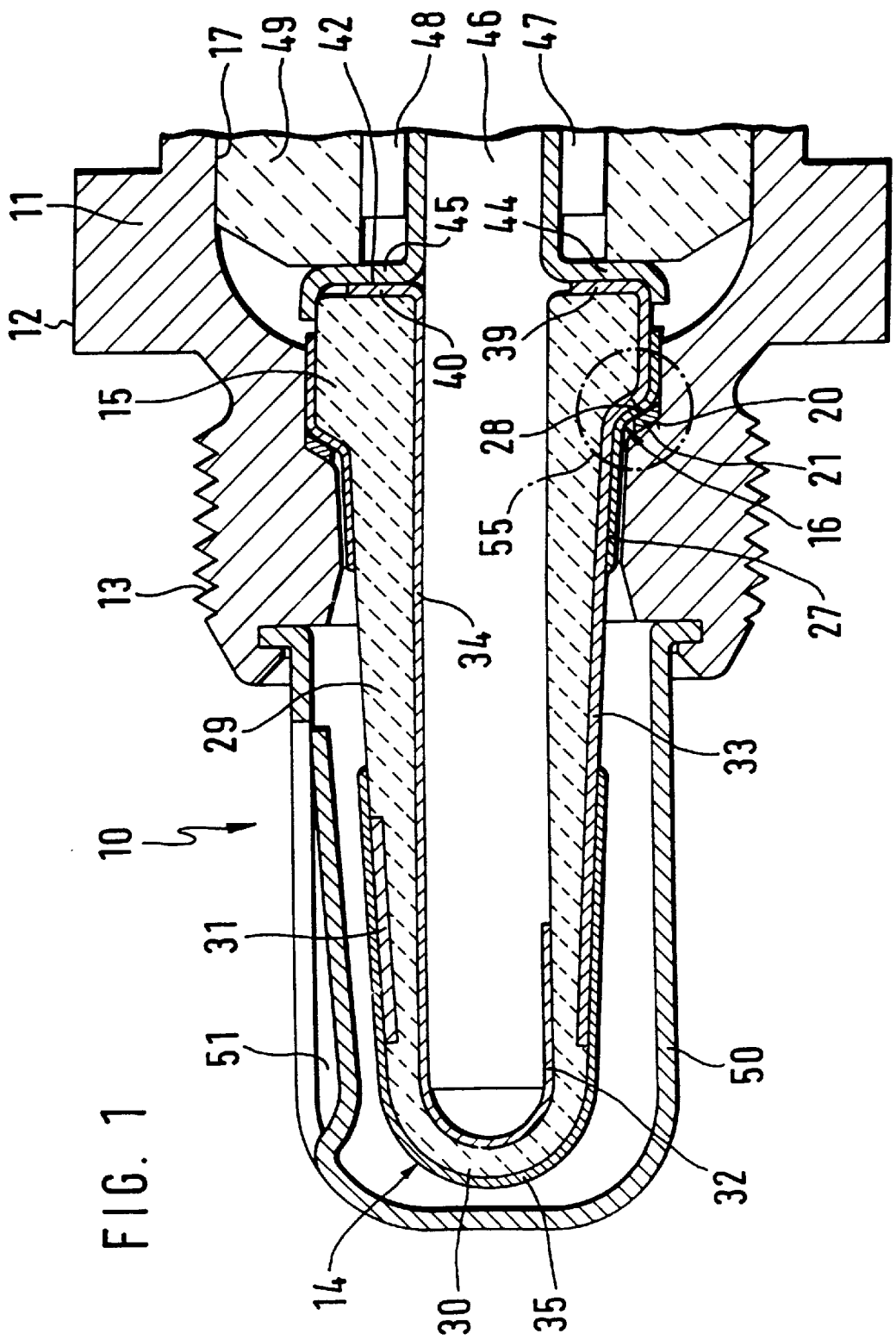
FIG. 1 shows a longitudinal section through the exhaust-gas portion of a sensor according to the present invention.

Electrochemical sensor 10 depicted in FIG. 1 has a metal housing 11 which has on its exterior a hex head 12 and threads 13 as attachment means for installation into a measured-gas tube (not depicted). Housing 11 has a longitudinal bore 17 with a sealing seat 20 which carries a sealing ring 21. A sensor element 14 having a shoulder 16 configured on a toroidal head 15 lies on sealing seat 20 equipped with sealing ring 21. A sealing surface 28 on the sensor-element side is formed on toroidal head 15 of sensor element 14 between sealing ring 21 and sensor element 14. Sealing seat 20 in turn forms a housing-side sealing surface. Sealing zone 55 which is constituted on sealing ring 21 is depicted at enlarged scale in FIG. 2.

In the present exemplary embodiment, sensor element 14 is an oxygen probe, known per se, which is used preferentially for measuring the oxygen partial pressure in exhaust gases. Sensor element 14 has a ceramic element 29 that may be embodied as a tubular solid electrolyte element 29 whose measurement-gas end section is closed off by a base 30. A film-like gas-permeable measurement electrode 31 is arranged on the exterior exposed to the measured gas, and a gas-permeable and film-like reference electrode 32, exposed to a reference gas (for example, air), is arranged on the side facing the interior. Measurement electrode 31 is connected by means of a measurement electrode conductor path 33 to a first electrode contact 39, and reference electrode 32 is connected by means of a reference electrode conductor path 34 to a second electrode contact 40. Electrode contacts 39, 40 are respectively located on an end surface 42 constituted by the open end of ceramic element 29. A porous protective layer 35 is laid over measurement electrode 31 and partially over measurement electrode conductor path 33. Electrodes 31, 32 and conductor paths 33, 34 are advantageously configured as cermet layers and co-sintered.

Sensor element 14, which projects out of longitudinal bore 17 of housing 11 at the measured-gas end, is surrounded at a distance by a protective tube 50 which possesses openings 51 for the entry and exit of the measured gas, and is held at the measured-gas end of housing 11. The interior of sensor element 14 is filled, for example, by a rod-shaped heating element 46 which is immobilized (not depicted) in a manner remote from the measured gas and is equipped with conductor terminals.

A first contact element 44 rests on first electrode contact 39, and a second contact element 45 on second electrode contact 40. Contact elements 44, 45 are shaped so that they rest against the rodshaped heating element 46 and are contacted by means of a measurement electrode terminal 47 and a reference electrode terminal 48. Contact is made to terminals 47, 48 with terminal cables (not depicted), which are guided outward to a measurement or control unit. In addition, an insulating sleeve 49 which preferably consists of a ceramic material is introduced into longitudinal bore 17 of housing 11. Insulating sleeve 49 is pushed onto contact elements 44, 45 by means of a mechanical means that is not depicted, thereby creating the electrical connection to electrode contacts 39, 40.

Figure 2:
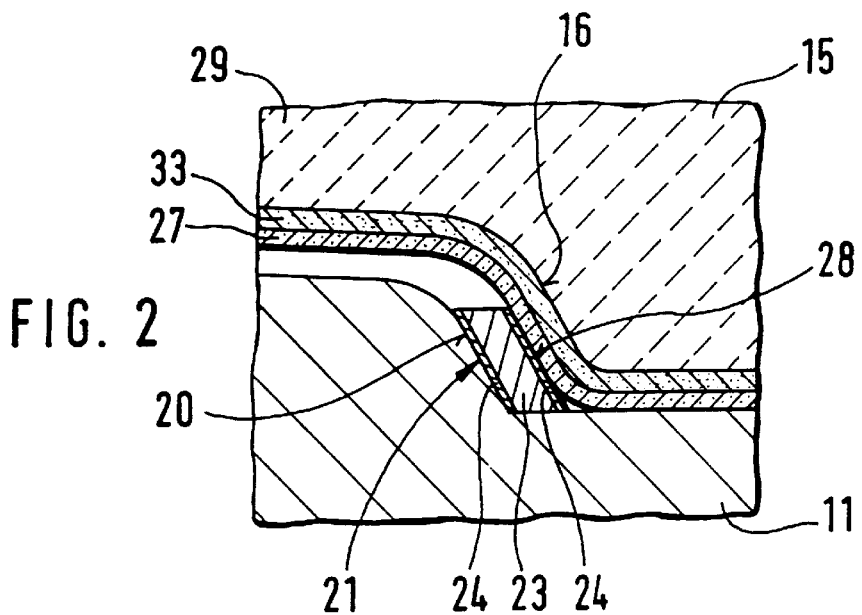
FIG. 2 shows an enlarged portion of a sealing zone as depicted in FIG. 1.

A clear depiction of sealing zone 55 between ceramic element 29 and housing 11 is evident from FIG. 2. According to FIG. 2, in order to protect conductor path 33, the latter is covered with an additional protective cover layer 27 in the region of sealing surface 28 on the sensor element side. Cover layer 27 possesses a layer thickness of 20 to 100 μm. In the present exemplary embodiment, cover layer 27 is applied over the entire region of conductor path 33 and around the periphery of ceramic element 29 which is adjacent to housing 11. It is, however, equally possible to limit cover layer 27 only to the region of sealing surface 28, or to extend cover layer 27 on the measured-gas side up to protective layer 35, which is advantageous because soiling due to soot and/or other conductive deposits from the exhaust gas is prevented. Protective layer 35 consists, for example, of plasma-sprayed magnesium spinel.

The material of cover layer 27 is selected to withstand the compressive forces of sealing ring 21 which occur when sensor element 14 is fitted into housing 11. Moreover, the material must be able to withstand application temperatures of up to 700 degrees C. This is achieved by the fact that a homogeneously distributed, crystalline, nonmetallic material forms a load-bearing protective structure in a glaze layer, and the transformation temperature of the glaze is above the application temperature. Possible materials are $Al_2O_3$, magnesium spinel, forsterite, MgO-stabilized $ZrO_2$, $Cr_2O_3$ and/or $Y_2O_3$-stabilized $ZrO_2$ with low stabilizer concentrations advantageously with a maximum of two-thirds of the stabilizer oxide used for full stabilization and having unstabilized $ZrO_2$ or $HfO_2$, or a mixture of these substances. An alkaline earth silicate, for example barium aluminum silicate, is used as the glass-forming material. Barium aluminum silicate has a coefficient of thermal expansion of $\geq 8.5*10^{-6}$ $K^{-1}$. Up to 30% of the $Ba^{2+}$ cations can be replaced by $Sr^{2+}$.

Figure 3:
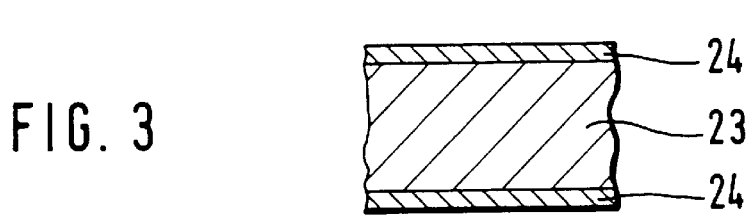
FIG. 3 shows a sealing element according to the present invention having a roll-clad copper layer applied to both sides thereof.

To achieve gas-tight attachment of sensor element 14 in housing 11, shoulder 16 configured at toroidal head 15 sits on housing 11 by means of sealing ring 21. In order to seal the interior of sensor element 14, sealing ring 21 consists, as shown in FIGS. 2 and 3, of a solid core 23, forming a support, made of an iron-chromium or iron-chromium-nickel alloy, preferably of iron-22/chromium-MM stainless steel at a thickness of approximately 0.5 mm, which is covered on each side by a roll-clad copper layer 24 that is at least 0.05 mm, preferably 0.1 to 0.2 mm thick. The roll-clad material is particularly impermeable to gas, water, and fuel because of its high densification.

Figure 4:
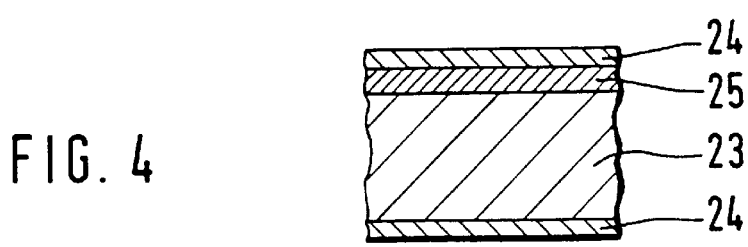
FIG. 4 shows the sealing element of the present invention provided with an additional roll-clad nickel layer applied beneath one of the roll-clad copper layers.
Figure 5:
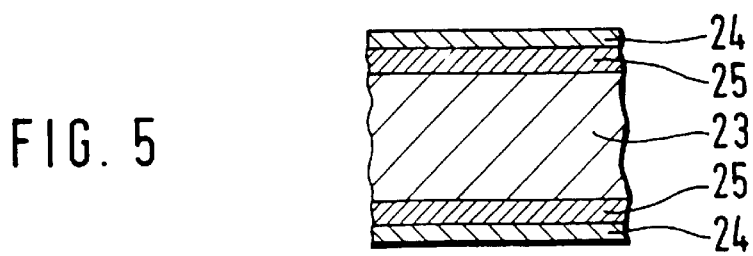
FIG. 5 shows the sealing element of the present invention provided with a roll-clad nickel layer applied beneath each of the two roll-clad copper layers.

An exemplary embodiment of sealing ring 21 which is built up from multiple different metal layers is shown in FIG. 4. Here an additional metal layer 25 of nickel is applied, for example, beneath one of the two roll-clad copper layers 24. Nickel layer 25 is also applied by roll-cladding. The thickness of nickel layer 25 is, for example, 0.1 mm to 0.2 mm. FIG. 5 shows a further exemplary embodiment of sealing ring 21 that is constructed from multiple different metal layers. Here an additional metal layer 25 of nickel is applied beneath each of the two roll-clad copper layers 24. Both additional nickel layers 25 are also applied by roll-cladding. The thickness of the additional nickel layers 25 is also approximately 0.1 mm.

In a further exemplary embodiment that is not depicted, a further metal layer of Ni or Pd is deposited, at a thickness of 0.1 to 1 μm, onto the roll-clad copper layer 24 in an electroless metallization method that is known per se. Sealing ring 21 is then heat-treated so that if the nickel layer is applied, the latter reacts with copper layer 24 located beneath it to form a layer of highly corrosion-resistant Monel metal.

What is claimed is:

1. A sensor for determining oxygen content in an exhaust gas of an internal combustion engine, comprising:
    a housing;
    a ceramic sensor element inserted into the housing; and
    a sealing element inserted into the housing, wherein the sealing element includes a metal support and at least one roll-clad metal layer provided on at least one surface of the metal support facing the ceramic sensor element, the sealing element sealing a space between the housing and the ceramic sensor.

2. The sensor according to claim 1, wherein the at least one roll-clad metal layer includes one of copper and a copper alloy.

3. The sensor according to claim 1, further comprising a nickel layer applied beneath the at least one roll-clad metal layer.

4. The sensor according to claim 1, further comprising an additional layer applied to the at least one roll-clad metal layer, wherein the additional layer includes one of Ni and Pd.

5. The sensor according to claim 1, wherein the at least one roll-clad metal layer includes:
    a first roll-clad metal layer provided on a surface of the sealing element contacting the ceramic sensor element, and
    a second roll-clad metal layer provided on a surface of the sealing element contacting the housing.

6. The sensor according to claim 5, further comprising at least one nickel layer arranged beneath at least one of the first roll-clad metal layer and the second roll-clad metal layer.

7. The sensor according to claim 6, wherein the at least one nickel layer has a maximum thickness of 0.2 mm.

8. The sensor according to claim 1, wherein the at least one roll-clad metal layer has a maximum layer thickness of 0.2 mm.

9. The sensor according to claim 1, wherein the metal support includes a sealing ring having a first surface and a second surface, the first surface facing the housing, the second surface facing the ceramic sensor element.

10. The sensor according to claim 9, wherein the at least one roll-clad metal layer is formed on at least one of the first surface and the second surface of the sealing ring.

11. The sensor according to claim 1, wherein the metal support is formed of at least one of a corrosion resistant steel alloy and a temperature resistant steel alloy.

12. The sensor according to claim 11, wherein the metal support is form of one of Fe—Cr, Fe—Cr—V, Fe—Cr—Mo, and Fe—Cr—Ni.

13. A method for manufacturing a sensor that determines oxygen content in an exhaust gas of an internal combustion engine, comprising the steps of:
    inserting a ceramic sensor element into a housing;
    providing at least one surface of a metal support of a sealing element with at least one roll-clad metal layer;
    inserting the sealing element into the housing such that the at least one surface of the metal support provided with the at least one roll-clad metal layer faces the ceramic sensor element and the sealing element seals a space between the housing and the ceramic sensor element; and
    applying a thermal treatment to the sensor to at least partially oxidize a surface of the at least one roll-clad metal layer.

* * * * *